United States Patent [19]

Lachke et al.

[11] Patent Number: 5,455,163
[45] Date of Patent: Oct. 3, 1995

[54] PROCESS FOR PRODUCING ALCOHOL

[75] Inventors: Anil H. Lachke; Arvind N. Kotasthane, both of Maharashtra; Sanjay S. Palnitkar, Pune, all of Ind.

[73] Assignee: Council Of Scientific & Industrial Research, New Delhi, Ind.

[21] Appl. No.: 219,821

[22] Filed: Mar. 30, 1994

[51] Int. Cl.$^6$ .................................. C12P 7/02; C12P 7/06
[52] U.S. Cl. ........................ 435/161; 435/155; 435/921
[58] Field of Search .................................. 435/161, 921, 435/155

[56] References Cited

U.S. PATENT DOCUMENTS 4,701,414 10/1987 Vandijken et al. ...................... 435/161

OTHER PUBLICATIONS

CA 108:148865(17) Prior et al "Biotech Lett 18(1)" pp. 337–342 (1988).

Biotech 87–13084 Roque–Malherbe et al "Biotech Lett 9, 9," pp. 640–642 (1987).

ATCC Catalogue Yeasts 18th Ed 1990 pp. 17–18 Candida Shehatae Jong et al Editor.

*Primary Examiner*—Herbert J. Lilling
*Attorney, Agent, or Firm*—Abelman, Frayne & Schwab

[57] ABSTRACT

A process for the production of alcohol by the fermentation of D-xylose employing the yeast *Canadida shehatae* in the presence of synthetic aluminosilicates of mineral faujasite structure zeolites of X or Y type or a combination thereof.

8 Claims, No Drawings

PROCESS FOR PRODUCING ALCOHOL

The present invention relates to a process for the production of alcohol, particularly ethanol. The present invention relates to the production of alcohols, with high yields by the fermentation of pentoses, more specifically D-xylose, employing the yeast *Candida shehatae* ATCC 22984. More specifically, the present invention relates to an improved fermentation process for the production of ethanol in high yields, the improvement comprising culturing of a D-xylose fermenting microorganism viz., *Candida shehatae* in a fermentation medium wherein synthetic aluminosilicates of mineral faujasite structure zeolites of X- or Y-type or the combination of both. In addition, to D-xylose the fermentation medium contains growth factors, salts and appropriate nitrogen source. For example, Yeast Nitrogen Base (YNB, Difco Products), 0.67%; or Potassium di hydrogen phosphate, 1.87%; Di ammonium hydrogen phosphate, 0.60%; Magnesium sulphate, 0.113%; and yeast extract, 0.37% (w/v). The initial pH of the medium is in between 4.5–5.0. Other inorganic and organic nitrogen sources can also be incorporated in the medium to provide 1.06 g nitrogen per litre. This includes, urea, peptone, yeast extracts, ammonium chloride, ammonium sulphate, and/or sodium nitrate.

Most of the components of the plant wastes have to be utilized to prevent environmental problems. Therefore efficient utilization of both the cellulosic as well as the hemicellulosic portions of the plant wastes is essential. Cellulose is made up of glucose units whereas hemicelluloses mainly consists of pentoses, the major fraction being D-xylose. Thus, D-xylose is the second most abundant sugar in the biosphere. Though glucose can be converted to other products using microorganisms, D-xylose can be slowly fermented by only a limited number of yeasts, namely *Candida shehatae, Pichia stipitis, Candida tropicalis*, and *Pachysolen tannophilus*.

In the prior art various methods are known for producing alcohol, especially ethanol, via fermentation employing immobilized microorganism (Ind. Pat. 157854, 1986, 32F 30 IX(1)) or using a continuous fermentation process (Ind. Pat. 150767, 1982, 32F 3c IX(1)) as well as using natural zeolites during alcohol fermentation [Rogue Malherbe et al, (1987) Biotechnol. Lett. 9, 640–642].

The conventional process for the manufacture of alcohol by fermentation cannot be applied to D-xylose fermentation. This is because only a few yeasts can produce ethanol from D-xylose with low yields under very different fermentation conditions. Comparatively, *Candida shehatae* is an efficient ethanol producer from D-xylose. [Du Preez J. C. and Prior B. A. (1985) Biotechnol. Lett. 7,241–246.]

However, as compared to D-glucose, the fermentation of D-xylose is a slow process and hence it is not suitable for industrial application. Further, the yields of ethanol from D-xylose are also low. In several laboratory experiments, the maximum production of ethanol from D-xylose was found to be in an approximate range of 30–70% of the theoretically attainable yield [Slininger et al, (1983) Biotechnol. Bioeng. 24, 371–384; Dekker R. F. H. (1983) Biotechnol. Lett. 4, 411–416]. Theoretically, 1 gm. of D-xylose should produce 0.51 gm of ethanol. However, when the fermentation is carried out under semiaerobic conditions, as in the present case, the theoretical yield is 0.41 gm of ethanol from 1.0 gm of D-xylose. This is because, D-xylose is used for growth as well as for the production of xylitol. Any improvement in fermentation conditions of D-xylose resulting in an enhanced ethanol production is necessary in order to reach toward theoretical attainable yields. This invention provides a potential use of synthetic aluminosilicate zeolites in small quantiites during fermentation to significantly enhance the rate and improve the production of ethanol using yeasts.

In the course of our investigations leading to the present invention, it was observed that incorporation of synthetic aluminosilicates at a relatively small percentage significantly improved the yields of ethanol under semiaerobic conditions. The zeolites, Na—Y and Na—Ca—X, when incorporated in the fermentation medium at 1.0% level, the yields of ethanol from D-xylose were 7.1 to 15.2% more than the practical yields in absence of any additive like Na—Y or Na—Ca—X.

Accordingly the present invention provides an improved process for producing alcohol, particularly ethanol, which comprises fermenting the yeast *Candida shehatae* having the Accession No ATCC 22984 in a fermenting medium in the presence of D-xylose and a catalyst selected from aluminosillicate of mineral faujasite structure, zeolites of X or Y type or a combination thereof at a temperature between 24° to 40° C. and for a period ranging from 24 to 96 hours.

The above said organism may be maintained on MXYP slants containing malt extract 0.3%, D-xylose 1.0%, yeast extract, 0.3%, peptone 0.5% and agar 2%.

In one embodiment of the process of the present invention the cells grown out of 3–5 day old slants were inoculated in the medium containing 2% D-xylose (w/v) and 0.67% Yeast Nitrogen Base (YNB, Difco) which was filter sterilized and further allowed to grow in Erlenmeyer flask mounted on a rotary shaker with a speed preferably between 100–250 rpm and most preferably vary in the temperature range of 28°–30° C.

In an other embodiment of the invention, the fermentation is effected in the presence of crystalline X or Y type aluminosilicate zeolites in their cationic exchanged forms and also in the basal medium comprising Yeast Nitrogen Base 0.67%, urea 76 mM and D-xylose 5–7.5%, where the weight percentage of zeolites is always above 0.5%. The composition of the aluminosilicate zeolites X or Y used as one of the ingredients in the medium in terms of their analytical composition is given in Table 1.

TABLE 1

| Synthetic Zeolites | Weight Percent Composition | | | | | |
|---|---|---|---|---|---|---|
| | | anhydrous | | | | |
| | LOI* | $SiO_2$ | $Al_2O_3$ | $Na_2O$ | CaO | Si/Al** |
| Na-Y | 28 | 63.60 | 23.77 | 12.60 | — | 2.275 |
| Na—Ca-X | 30 | 55.80 | 32.93 | 5.11 | 6.10 | 1.440 |

*LOI = Loss on ignition,
**mole ratios

According to this invention, it is also possible to obtain high yields that is more than 5–15% above the practically attainable yields of ethanol from D-xylose in a relatively short duration. This can be best achieved by incorporating in the medium synthetic sodium-Y or sodium-calcium-X type aluminosilicate zeolites. The presence of an exchanged derivative of either Na—Ca—X or Na—Y or the combination of both these zeolites in the fermentation medium renders beneficial effects on ethanol production.

The synthetic zeolites in their dehydrated forms can be made by calcining the as-made and exchanged zeolites in an electrically heated muffle furnace in the temperature range between 250°–400° C., most preferably between 325°–350° C. for a fixed period of 5 hours and then cooling down to a temperature up to about 75°–69° C. and then storing the said activated zeolites under saturated ammonium chloride solution at room temperature for at least 24 hours prior to the actual use made in the fermentation medium.

According to this invention, the maintenance of steady-state concentration of a fermentable medium in the presence of Na—Y or Na—Ca—X zeolites in the fermentor was compatible with a significant high ethanol productivity and the above said yeast *Candida shehatae* gives the following major advantages:

1. The concentration of the fermentable sugar in the medium was between 4–9% which showed the ethanol yields between 1.41 to 2.65 (w/v). (Refer to Table 2, Examples 3–7).

2. The presence of 0.5–1.5% aliminosilicate zeolites, especially the Na and Ca exchanged X and Y types, showed an increase the yield and the maximum ethanol production rate. (Refer to Table 2, Examples 3–7).

3. *Candida shehatae*, as mentioned earlier, is one of the most promising yeast that is able to ferment pentoses, especially D-xylose, in good yields and rates.

The present invention is illustrated in the examples given below which should not however be construed to limit the scope of the invention.

EXAMPLE 1

*Candida shehatae* ATCC 22984 was routinely maintained on MXYP slants (malt extract, 0.3%; D-xylose, 1.0%; yeast extract, 0.3 peptone, 0.5%; agar, 2%). It was cultivated in a liquid medium (125 ml medium in a 250 ml Erlenmeyer flask) containing 3% D-xylose and 0.67% Yeast Nitrogen Base (YNB) (Difco). Additional urea was added to give a final nitrogen content of 20 mM. D-Xylose was autoclaved separately and the YNB was filter sterilized. The flasks were incubated at 30° C. and 180 rpm for 48 h.

The fermentation medium contained D-xylose, urea to provide 76 mM nitrogen, and, 0.67% Yeast Nitrogen Base (prepared according to the Difco manual). Fermentation was carried out in 500 ml Erlenmeyer flasks containing 250 ml medium and inoculated with 5% cells (wet weight). The initial pH of the medium was 4.5±0.1. Samples were collected periodically for analysis. D-xylose, xylitol and ethanol were quantified by HPLC (HP model 1082 B with a RI detector and HP area integrator) on a Waters Sugars-Pak column with deionized water at 75° C. as the eluent.

When the fermentation was carried out at initial D-xylose concentrations between 1–12% and shaking speed between 0–300 rpm, at temperatures between 20°–37° C., it was found that a D-xylose concentration of 7.5% was optimum with the fermentation carried out at 28° C. and shaking speed of 200 rpm. The fermentation was carried out in 13 Erlenmeyer flasks. Under these conditions, 87.5 g ethanol was produced from 250 g D-xylose. Thus, it is 0.30 g/g yield of ethanol from D-xylose which is 68.6% of the theoretically possible yield. Ethanol was recovered by distillation whenever necessary for analysis.

EXAMPLE 2

*Candida shehatae* ATCC 22984 was routinely maintained on MXYP slants (malt extract, 0.3%; D-xylose, 1.0%; yeast extract, 0.3%; peptone, 0.5%; agar, 2%). It was cultivated in a liquid medium (125 ml medium in 250 ml Erlenmeyer flasks) containing 3% D-xylose and 0.67% Yeast Nitrogen Base (YNB, Difco). Additional urea was added to give a final nitrogen content of 20 mM. D-xylose was autoclaved separately and YNB was filter sterilized. The flasks were incubated at 30° C. and 180 rpm for 48 h. The fermentation medium contained D-xylose, urea to provide 76 mM nitrogen, and, 0.76% Yeast Nitrogen Base (prepared according to the Difco manual). Fermentation was carried out in 500 ml Erleyenmeyer flasks containing 259 ml medium and inoculated with 5% cells (wet weight). The initial pH of the medium was 4.5±0.1. Samples were collected periodically to estimate D-xylose, xylitol and ethanol by HPLC (HP model 1082 B with a RI detector and HP area integrator) on a Water Sugar-Pak column with deionized water at 75° C. as the eluent.

The fermentation was carried out with 1.0% activated Na—Ca—X and Na—Y in the fermentation medium on the total basis. 97.5 g ethanol at an initial concentration of D-xylose between 1 to 12% and a shaking speed between 0–300 rpm, at temperature between 20°–37° C. It was found that a D-xylose concentration of 7.5% was optimum with the fermentation carried out at 28° C. and a shaking of 200 rpm. This experiment was performed in 13 Erlenmeyer flasks. Under these conditions, 97.5 g ethanol was produced from 250 g D-xylose. Thus, 0.39 g/g of ethanol was obtained under the given experimental conditions. This yield is 76.5% of the theoretically possible yield of ethanol from D-xylose.

Only a small amount of Na—Ca—X and Na—Y are needed for the practice of this invention. Generally, from about 0.5% to about 1.5% is sufficient. We prefer, however, to use 1.0% w/v of Na—Ca—X and/or Na—Y zeolites.

TABLE 2

Incorporation of 1.0% Na-Y or 1.0% Na—Ca-X (w/v) in the fermentation medium* and its effect on the production of ethanol from different concentrations of D-Xylose by *Candida Shehatae* ATCC 22984
[Fermentation period 48 h]

| Examples | D-Xylose [% (w/v)] | Theoretical** yield of Ethanol (w/v) | Practical yield of Ethanol [% (w/v)] | Ethanol yield in presence of Na—Ca-X (1%) or Na-Y (1%) [% (w/v)] | Increase in yield of Ethanol over practical yield [%] |
|---|---|---|---|---|---|
| 3 | 4.0 | 2.04 | 1.28 | 1.41–1.45 | 10.2–13.2 |
| 4 | 5.0 | 2.55 | 1.65 | 1.75–1.85 | 9.0–12.1 |
| 5 | 6.0 | 3.06 | 1.92 | 2.20–2.22 | 14.6–15.6 |
| 6 | 7.5 | 3.83 | 2.30 | 2.60–2.65 | 13.0–15.2 |
| 7 | 9.0 | 4.60 | 2.38 | 2.55–2.65 | 7.1–11.3 |

*Medium contains: Yeast Nitrogen Base 0.67% and urea 76 mM. (Both were filtered through 0.22 micron membrane separately).

TABLE 2-continued

Incorporation of 1.0% Na-Y or 1.0% Na—Ca-X (w/v) in the fermentation medium* and its effect on the production of ethanol from different concentrations of D-Xylose by *Candida Shehatae* ATCC 22984
[Fermentation period 48 h]

| Examples | D-Xylose [% (w/v)] | Theoretical** yield of Ethanol (w/v) | Practical yield of Ethanol [% (w/v)] | Ethanol yield in presence of Na—Ca-X (1%) or Na-Y (1%) [% (w/v)] | Increase in yield of Ethanol over practical yield [%] |
|---|---|---|---|---|---|

**1 gm D-Xylose should produce 0.51 gm ethanol under anaerobic conditions. [D-Xylose is used for growth and for production of xylitol also. Under semiaerobic conditions, the theoretical yield of ethanol is 0.41 g/g]

We claim:

1. A process of producing alcohol, which comprises fermenting the yeast *Candida shehatae* having the Accession no ATCC 22984 in a fermenting medium in the presence of D-xylose and a catalyst selected from aluminosilicate of mineral faujasite structure zeolites X or Y type or a combination thereof at a temperature between 24° to 40° C. and for a period ranging from 24 to 96 hours.

2. A process as claimed in claim 1 wherein the percent weight/volume concentration of synthetic aluminosilicate zeolite used is in the range of 0.5–1.0% (w/v).

3. A process as claimed in claim 1 wherein the synthetic aluminosilicate zeolite is selected from Na—Ca—X or Na—Y type aluminosilicate zeolites.

4. A process as claimed in claim 1 wherein the zeolites are in their sodium, calcium, forms without any further ionic exchange and their weight ratio being above 0.5%.

5. A process as claimed in claim 1 wherein the fermentation medium has initial pH of 5.5±0.1 and final pH of 4.5±0.1.

6. A process as claimed in claim 1 wherein the fermentation was carried out under semiaerobic conditions at 28° C.

7. A process as claimed in claim 1 wherein the fermentation medium consists of Yeast Nitrogen Base 0.67%, urea 76 mM, D-xylose 5.0 to 7.5%.

8. A process as claimed in claim 1 wherein the alcohol is ethanol.

* * * * *